(12) United States Patent
Nolan et al.

(10) Patent No.: US 6,969,584 B2
(45) Date of Patent: Nov. 29, 2005

(54) COMBINATORIAL ENZYMATIC COMPLEXES

(75) Inventors: Garry P. Nolan, Menlo Park, CA (US); Donald Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 08/873,601

(22) Filed: Jun. 12, 1997

(65) Prior Publication Data

US 2002/0064798 A1 May 30, 2002

(51) Int. Cl.⁷ ............................................. C12Q 1/68
(52) U.S. Cl. .................. 435/6; 435/4; 435/5; 435/7.2; 435/7.4; 435/7.91; 435/DIG. 3; 435/DIG. 2
(58) Field of Search ........................ 435/7.91, 7.4, 435/7.2, 6, 4, DIG. 3, DIG. 2, 7.1, 440, 45.5, 471, 476, 29, 68.1, 175, 263, 262

(56) References Cited

U.S. PATENT DOCUMENTS

| | | | | |
|---|---|---|---|---|
| 5,672,491 A | * | 9/1997 | Khosla et al. | 435/148 |
| 5,837,458 A | * | 11/1998 | Minshull et al. | 435/6 |
| 6,365,344 B1 | * | 4/2002 | Nolan et al. | 435/6 |
| 6,391,594 B1 | * | 5/2002 | Khosla et al. | 435/91.4 |

FOREIGN PATENT DOCUMENTS

| | | | |
|---|---|---|---|
| WO | 92/07085 | | 4/1992 |
| WO | WO 97/14789 | * | 4/1992 |
| WO | WO 95/08548 | * | 3/1995 |
| WO | 96/34112 | | 10/1996 |
| WO | 96/38553 | | 12/1996 |
| WO | 96/40902 | | 12/1996 |
| WO | 97/27212 | | 7/1997 |
| WO | 97/27213 | | 7/1997 |

OTHER PUBLICATIONS

Miceli et al, Drug Design and Discovery, 1996, 13, 95–105.*
Pikus et al. Biochemistry (1996) 35(28):9106–9119.*
Srere, P.A. (1987) Ann. Rev. Biochem. 56:89–91.*
Horowitz, M.S., Adenoviridae and Their Replication. In "Fundemental Virology 2nd Edition" Fields et al. Eds. Raven Press, New York, pp. 771–813, 1991.*
Padmanabhan et al. Three basic regions in adenovirus DNA polymerase interact differentially depending on the protein context to function as bipartite nuclear localization signals, New Biology vol. 3 No. 11, pp. 1074–1088 (abstract only provided), 1991.*
Ricard et al., Eur J. Biochem, vol. 226, pp 993–998, 1994.*
Roessner, et al., "Achieving natural product synthesis and diversity via catalytic networking ex vivo," *Chemistry & Biology* 3(5):325–330 (1996).
Wong, et al., "Enzymes in Organic Synthesis: Application to the Problems of Carbohydrate Recognition (Part 2)," *Angew. Chem. Int. Ed. Engi.* 34:521–546 (1995).
Eschenmoser, "Vitamin $B_{12}$: Experiments Concerning the Origin of Its Molecular Structure," *Angew. Chem. Int. Ed. Engi.* 27:6–39 (1988).
Scott, "Genetically Engineered Synthesis of Natural Products," *Journal of Natural Products* 57(5):557–573 (1994).
Scott, "Towards the genetically engineered synthesis of natural products," *Chemistry & Biology* Introductory issue (1994).
Roessner, et al., "Genetically engineered synthesis of precorrin-6x and the complete corrinoid, hydrogenobyrinic acid, an advanced precursor of vitamin $B_{12}$," *Chemistry & Biology* 1:119–124 (1994).
Wiesmann, et al., "Polyketide synthesis in vitro on a modular polyketide synthase," *Chemistry & Biology* 2:583–589 (1995).
Fessner, et al., "Artificial Metabolisms for the Asymmetric One–Pot Synthesis of Branched–Chain Saccharides," *Angew. Chem. Int. Ed. Engl.*, 31(5):614–616 (1992).
Kren, et al., "A Multienzyme System for a One–Pot Synthesis of Sialyl T–Antigen," *Angew. Chem. Int. Ed. Engi.* 34(8):893–895 (1995).
Shen, et al., "Enzymatic Synthesis of a Bacterial Polyketide from Acetyl and Malonyl Coenzyme A," *Science* 262:1535–1540 (1993).
Wong, et al., "Practical Enzymatic Syntheses of Ribulose 1,5–Bisphosphate and Ribose 5–Phosphate," *J. Am. Chem. Soc.* 102:7938–7939 (1980).
Roessner, et al., "Overexpression in *Escherichia coli* of 12 Vitamin $B_{12}$ Biosynthetic Enzyme," *Protein Expression and Purification* 6:155–163 (1995).
Marumo, et al., "Enzymatic synthesis and isolation of thymidine diphosphate-6–deoxy–D–xylo–4–hexulose and thymidine diphosphate–L–rhamnose," *Biochem.* 204:539–545 (1992).
Lindqvist, et al., "in vitro synthesis of CDP-D-abequose using *Salmonella* enzymes of cloned *rfb* genes," *Eur. J. Biochem.* 225:863–872 (1994).
Roessner, et al., "Expression of 9 *Salmonella typhimurium* enzymes for cobinamide synthesis," *FEBS Letters* 301(1):73–78 (1992).
Gonzalez, et al., "Design of A Reusable Enzymatic System for the Preparation of Porphyrins of Biological Interest," *Bioorganic & Medicinal Chemistry Letters* 4(5):743–746 (1994).
Duggan, et al., "Enzymatic Synthesis of (6R)– and (6S)–Fluoroshikimic Acids," *Bioorganic & Medicinal Chemistry Letters* 5(20):2347–2352 (1995).

* cited by examiner

Primary Examiner—T. D. Wessendorf
(74) Attorney, Agent, or Firm—James S. Keddie; Carol L. Francis; James J. Diehl

(57) ABSTRACT

The invention relates to the formation of novel in vivo combinatorial enzyme complexes for use in screening candidate drug agents for bioactivity.

2 Claims, 5 Drawing Sheets

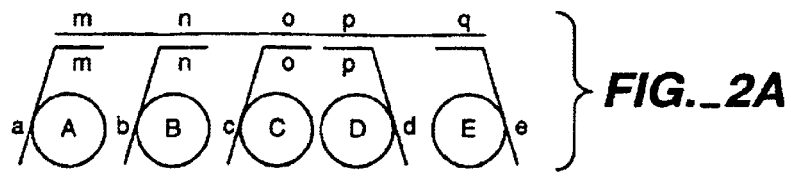 FIG._2A
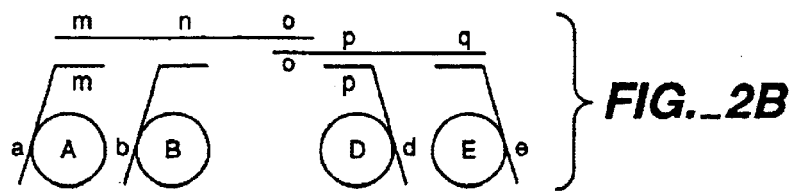 FIG._2B
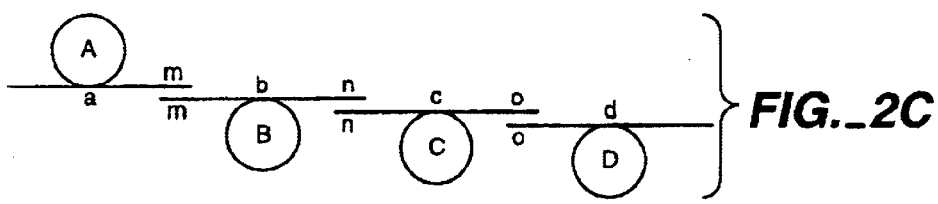 FIG._2C
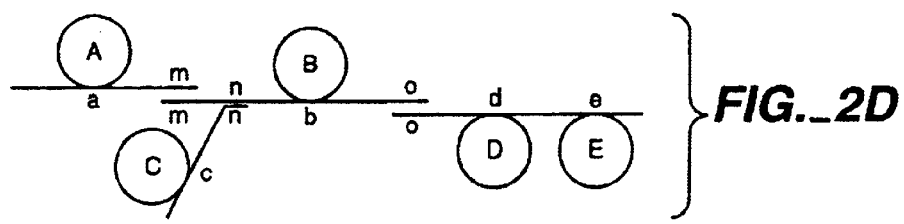 FIG._2D
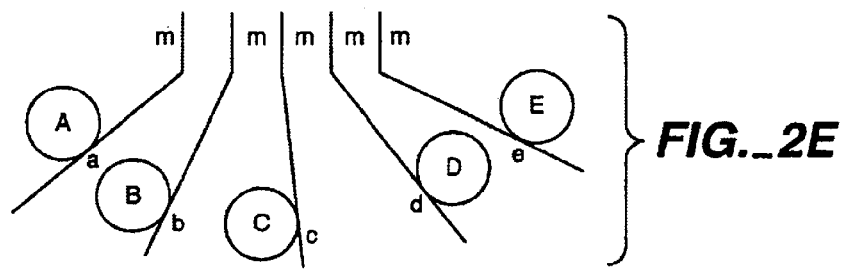 FIG._2E
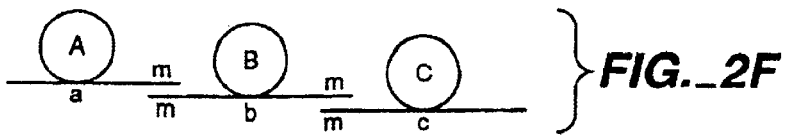 FIG._2F

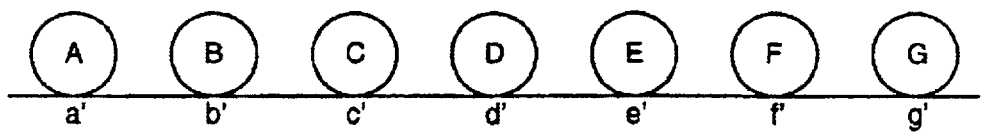
FIG._3
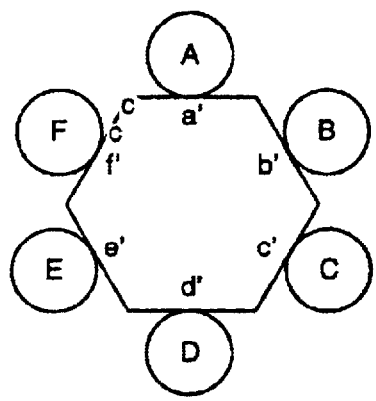
FIG._4A
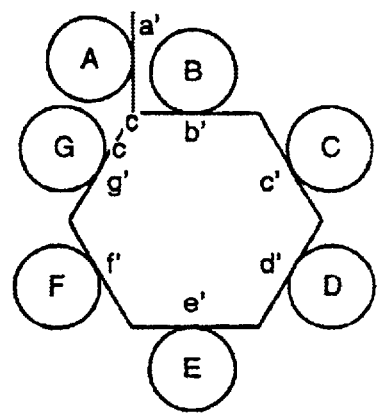
FIG._4B
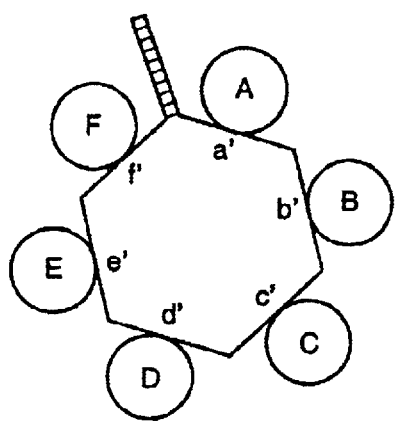
FIG._4C
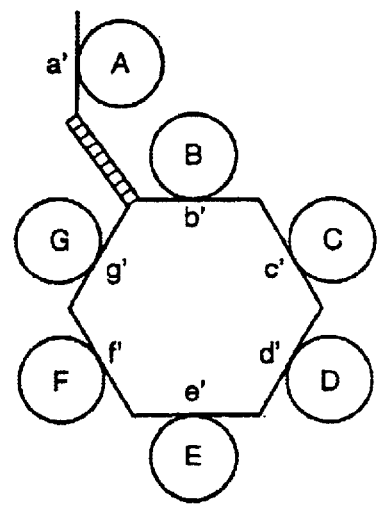
FIG._4D

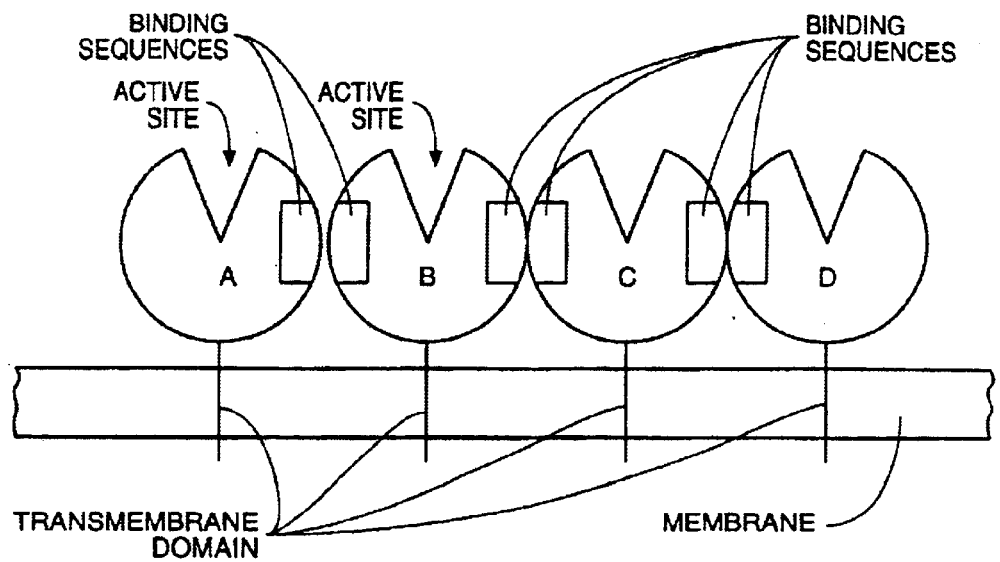
FIG._5A
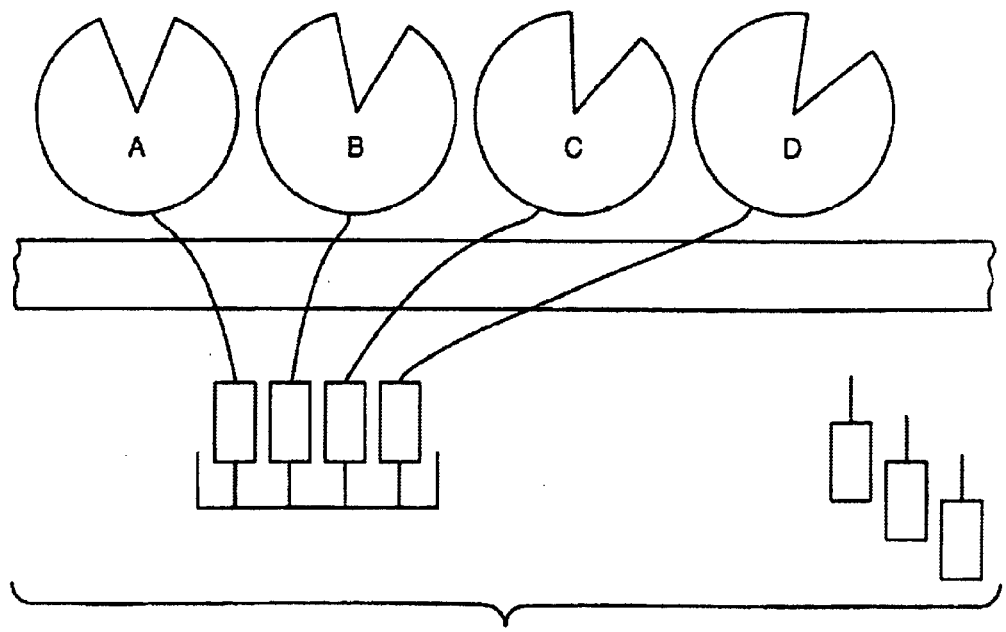
FIG._5B

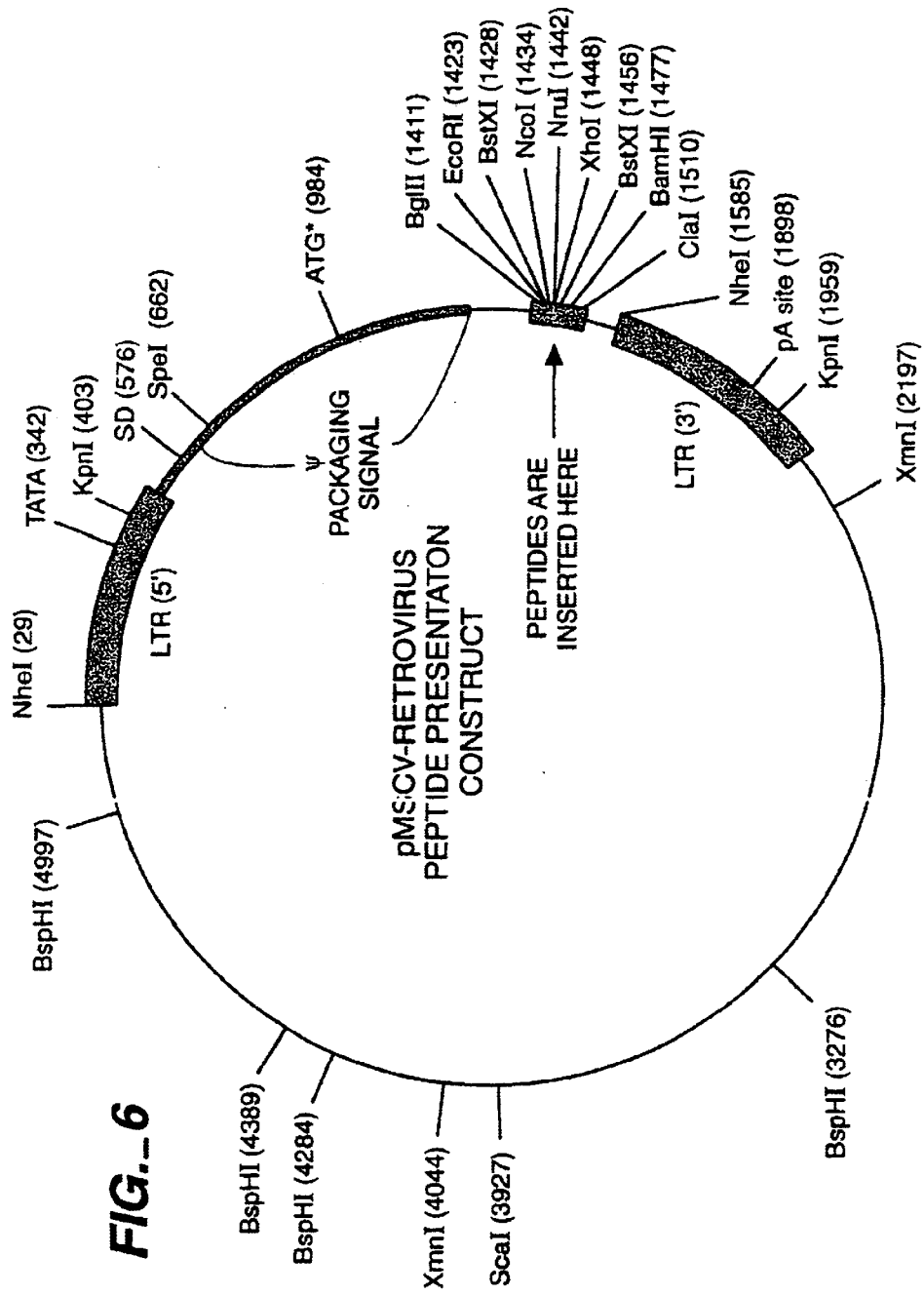
FIG._6

SEQUENCE LISTING

<160> NUMBER OF SEQ ID NOS: 35

<210> SEQ ID NO 1
<211> LENGTH: 61

```
<212> TYPE: PRT
<213> ORGANISM: Artificial Sequence
<220> FEATURE:
<223> OTHER INFORMATION: Description of Artificial Sequence: Synthetic

<400> SEQUENCE: 1

Met Gly Cys Ala Ala Leu Glu Ser Glu Val Ser Ala Leu Glu Ser Glu
 1               5                  10                  15
Val Ala Ser Leu Glu Ser Glu Val Ala Ala Leu Gly Arg Gly Asp Met
             20                  25                  30
Pro Leu Ala Ala Val Lys Ser Lys Leu Ser Ala Val Lys Ser Lys Leu
         35                  40                  45
Ala Ser Val Lys Ser Lys Leu Ala Ala Cys Gly Pro Pro
     50                  55                  60

<210> SEQ ID NO 2
<211> LENGTH: 69
<212> TYPE: PRT
<213> ORGANISM: Artificial Sequence
<220> FEATURE:
<223> OTHER INFORMATION: Description of Artificial Sequence: Synthetic

<400> SEQUENCE: 2

Met Gly Arg Asn Ser Gln Ala Thr Ser Gly Phe Thr Phe Ser His Phe
 1               5                  10                  15
Tyr Met Glu Trp Val Arg Gly Gly Glu Tyr Ile Ala Ala Ser Arg His
             20                  25                  30
Lys His Asn Lys Tyr Thr Thr Glu Tyr Ser Ala Ser Val Lys Gly Arg
         35                  40                  45
Tyr Ile Val Ser Arg Asp Thr Ser Gln Ser Ile Leu Tyr Leu Gln Lys
     50                  55                  60
Lys Lys Gly Pro Pro
 65

<210> SEQ ID NO 3
<211> LENGTH: 7
<212> TYPE: PRT
<213> ORGANISM: SV 40

<400> SEQUENCE: 3

Pro Lys Lys Lys Arg Lys Val
 1               5

<210> SEQ ID NO 4
<211> LENGTH: 6
<212> TYPE: PRT
<213> ORGANISM: Homo sapiens

<400> SEQUENCE: 4

Ala Arg Arg Arg Arg Pro
 1               5

<210> SEQ ID NO 5
<211> LENGTH: 10
<212> TYPE: PRT
<213> ORGANISM: Homo sapiens

<400> SEQUENCE: 5

Glu Glu Val Gln Arg Lys Arg Gln Lys Leu
 1               5                  10

<210> SEQ ID NO 6
```

```
<211> LENGTH: 9
<212> TYPE: PRT
<213> ORGANISM: Homo sapiens

<400> SEQUENCE: 6

Glu Glu Lys Arg Lys Arg Thr Tyr Glu
 1               5

<210> SEQ ID NO 7
<211> LENGTH: 20
<212> TYPE: PRT
<213> ORGANISM: Xenopus laevis

<400> SEQUENCE: 7

Ala Val Lys Arg Pro Ala Ala Thr Lys Lys Ala Gly Gln Ala Lys Lys
 1               5                  10                  15

Lys Lys Leu Asp
            20

<210> SEQ ID NO 8
<211> LENGTH: 31
<212> TYPE: PRT
<213> ORGANISM: Homo sapiens

<400> SEQUENCE: 8

Met Ala Ser Pro Leu Thr Arg Phe Leu Ser Leu Asn Leu Leu Leu Leu
 1               5                  10                  15

Gly Glu Ser Ile Leu Gly Ser Gly Glu Ala Lys Pro Gln Ala Pro
            20                  25                  30

<210> SEQ ID NO 9
<211> LENGTH: 21
<212> TYPE: PRT
<213> ORGANISM: Homo sapiens

<400> SEQUENCE: 9

Met Ser Ser Phe Gly Tyr Arg Thr Leu Thr Val Ala Leu Phe Thr Leu
 1               5                  10                  15

Ile Cys Cys Pro Gly
            20

<210> SEQ ID NO 10
<211> LENGTH: 51
<212> TYPE: PRT
<213> ORGANISM: Homo sapiens

<400> SEQUENCE: 10

Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
            35                  40                  45

His Ser Arg
    50

<210> SEQ ID NO 11
<211> LENGTH: 33
<212> TYPE: PRT
<213> ORGANISM: Homo sapiens

<400> SEQUENCE: 11
```

```
Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
            20                  25                  30

Arg

<210> SEQ ID NO 12
<211> LENGTH: 37
<212> TYPE: PRT
<213> ORGANISM: Unknown
<220> FEATURE:
<223> OTHER INFORMATION: Description of Unknown Organism: UNKNOWN

<400> SEQUENCE: 12

Pro Asn Lys Gly Ser Gly Thr Thr Ser Gly Thr Thr Arg Leu Leu Ser
 1               5                  10                  15

Gly His Thr Cys Phe Thr Leu Thr Gly Leu Leu Gly Thr Leu Val Thr
            20                  25                  30

Met Gly Leu Leu Thr
            35

<210> SEQ ID NO 13
<211> LENGTH: 14
<212> TYPE: PRT
<213> ORGANISM: Unknown
<220> FEATURE:
<223> OTHER INFORMATION: Description of Unknown Organism: UNKNOWN

<400> SEQUENCE: 13

Met Gly Ser Ser Lys Ser Lys Pro Lys Asp Pro Ser Gln Arg
 1               5                  10

<210> SEQ ID NO 14
<211> LENGTH: 26
<212> TYPE: PRT
<213> ORGANISM: Unknown
<220> FEATURE:
<223> OTHER INFORMATION: Description of Unknown Organism: UNKNOWN

<400> SEQUENCE: 14

Leu Leu Gln Arg Leu Phe Ser Arg Gln Asp Cys Cys Gly Asn Cys Ser
 1               5                  10                  15

Asp Ser Glu Glu Glu Leu Pro Thr Arg Leu
            20                  25

<210> SEQ ID NO 15
<211> LENGTH: 20
<212> TYPE: PRT
<213> ORGANISM: Unknown
<220> FEATURE:
<223> OTHER INFORMATION: Description of Unknown Organism: UNKNOWN

<400> SEQUENCE: 15

Lys Gln Phe Arg Asn Cys Met Leu Thr Ser Leu Cys Cys Gly Lys Asn
 1               5                  10                  15

Pro Leu Gly Asp
            20

<210> SEQ ID NO 16
<211> LENGTH: 19
<212> TYPE: PRT
<213> ORGANISM: Unknown
<220> FEATURE:
<223> OTHER INFORMATION: Description of Unknown Organism: UNKNOWN
```

-continued

```
<400> SEQUENCE: 16

Leu Asn Pro Pro Asp Glu Ser Gly Pro Gly Cys Met Ser Cys Lys Cys
  1               5                  10                  15

Val Leu Ser

<210> SEQ ID NO 17
<211> LENGTH: 5
<212> TYPE: PRT
<213> ORGANISM: Unknown
<220> FEATURE:
<223> OTHER INFORMATION: Description of Unknown Organism: UNKNOWN

<400> SEQUENCE: 17

Lys Phe Glu Arg Gln
  1               5

<210> SEQ ID NO 18
<211> LENGTH: 36
<212> TYPE: PRT
<213> ORGANISM: Unknown
<220> FEATURE:
<223> OTHER INFORMATION: Description of Unknown Organism: UNKNOWN

<400> SEQUENCE: 18

Met Leu Ile Pro Ile Ala Gly Phe Phe Ala Leu Ala Gly Leu Val Leu
  1               5                  10                  15

Ile Val Leu Ile Ala Tyr Leu Ile Gly Arg Lys Arg Ser His Ala Gly
                 20                  25                  30

Tyr Gln Thr Ile
         35

<210> SEQ ID NO 19
<211> LENGTH: 35
<212> TYPE: PRT
<213> ORGANISM: Unknown
<220> FEATURE:
<223> OTHER INFORMATION: Description of Unknown Organism: UNKNOWN

<400> SEQUENCE: 19

Leu Val Pro Ile Ala Val Gly Ala Ala Leu Ala Gly Val Leu Ile Leu
  1               5                  10                  15

Val Leu Leu Ala Tyr Phe Ile Gly Leu Lys His His Ala Gly Tyr
                 20                  25                  30

Glu Gln Phe
         35

<210> SEQ ID NO 20
<211> LENGTH: 27
<212> TYPE: PRT
<213> ORGANISM: Saccharomyces cerevisiae

<400> SEQUENCE: 20

Met Leu Arg Thr Ser Ser Leu Phe Thr Arg Arg Val Gln Pro Ser Leu
  1               5                  10                  15

Phe Ser Arg Asn Ile Leu Arg Leu Gln Ser Thr
                 20                  25

<210> SEQ ID NO 21
<211> LENGTH: 25
<212> TYPE: PRT
<213> ORGANISM: Saccharomyces cerevisiae
```

```
<400> SEQUENCE: 21

Met Leu Ser Leu Arg Gln Ser Ile Arg Phe Phe Lys Pro Ala Thr Arg
 1               5                  10                  15

Thr Leu Cys Ser Ser Arg Tyr Leu Leu
            20                  25

<210> SEQ ID NO 22
<211> LENGTH: 64
<212> TYPE: PRT
<213> ORGANISM: Saccharomyces cerevisiae

<400> SEQUENCE: 22

Met Phe Ser Met Leu Ser Lys Arg Trp Ala Gln Arg Thr Leu Ser Lys
 1               5                  10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 23
<211> LENGTH: 41
<212> TYPE: PRT
<213> ORGANISM: Saccharomyces cerevisiae

<400> SEQUENCE: 23

Met Lys Ser Phe Ile Thr Arg Asn Lys Thr Ala Ile Leu Ala Thr Val
 1               5                  10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40

<210> SEQ ID NO 24
<211> LENGTH: 4
<212> TYPE: PRT
<213> ORGANISM: Unknown
<220> FEATURE:
<223> OTHER INFORMATION: Description of Unknown Organism: UNKNOWN

<400> SEQUENCE: 24

Lys Asp Glu Leu
 1

<210> SEQ ID NO 25
<211> LENGTH: 15
<212> TYPE: PRT
<213> ORGANISM: ADENOVIRUS

<400> SEQUENCE: 25

Leu Tyr Leu Ser Arg Arg Ser Phe Ile Asp Glu Lys Lys Met Pro
 1               5                  10                  15

<210> SEQ ID NO 26
<211> LENGTH: 19
<212> TYPE: PRT
<213> ORGANISM: Unknown
<220> FEATURE:
<223> OTHER INFORMATION: Description of Unknown Organism: UNKNOWN

<400> SEQUENCE: 26
```

Leu Asn Pro Pro Asp Glu Ser Gly Pro Gly Cys Met Ser Cys Lys Cys
 1               5                  10                  15

Val Leu Ser

<210> SEQ ID NO 27
<211> LENGTH: 15
<212> TYPE: PRT
<213> ORGANISM: Unknown
<220> FEATURE:
<223> OTHER INFORMATION: Description of Unknown Organism: UNKNOWN

<400> SEQUENCE: 27

Leu Thr Glu Pro Thr Gln Pro Thr Arg Asn Gln Cys Cys Ser Asn
 1               5                  10                  15

<210> SEQ ID NO 28
<211> LENGTH: 9
<212> TYPE: PRT
<213> ORGANISM: Unknown
<220> FEATURE:
<223> OTHER INFORMATION: Description of Unknown Organism: UNKNOWN

<400> SEQUENCE: 28

Arg Thr Ala Leu Gly Asp Ile Gly Asn
 1               5

<210> SEQ ID NO 29
<211> LENGTH: 20
<212> TYPE: PRT
<213> ORGANISM: Homo sapiens

<400> SEQUENCE: 29

Met Tyr Arg Met Gln Leu Leu Ser Cys Ile Ala Leu Ser Leu Ala Leu
 1               5                  10                  15

Val Thr Asn Ser
            20

<210> SEQ ID NO 30
<211> LENGTH: 29
<212> TYPE: PRT
<213> ORGANISM: Homo sapiens

<400> SEQUENCE: 30

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr
            20                  25

<210> SEQ ID NO 31
<211> LENGTH: 27
<212> TYPE: PRT
<213> ORGANISM: Homo sapiens

<400> SEQUENCE: 31

Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn
            20                  25

<210> SEQ ID NO 32
<211> LENGTH: 18
<212> TYPE: PRT
<213> ORGANISM: Influenza virus -continued

```
<400> SEQUENCE: 32

Met Lys Ala Lys Leu Leu Val Leu Leu Tyr Ala Phe Val Ala Gly Asp
 1               5                  10                  15

Gln Ile

<210> SEQ ID NO 33
<211> LENGTH: 24
<212> TYPE: PRT
<213> ORGANISM: Homo sapiens

<400> SEQUENCE: 33

Met Gly Leu Thr Ser Gln Leu Leu Pro Pro Leu Phe Phe Leu Leu Ala
 1               5                  10                  15

Cys Ala Gly Asn Phe Val His Gly
            20

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: SYNTHETIC

<400> SEQUENCE: 34

Gly Ser Gly Gly Ser
 1               5

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: SYNTHETIC

<400> SEQUENCE: 35

Gly Gly Gly Ser
 1
```

COMBINATORIAL ENZYMATIC COMPLEXES

FIELD OF THE INVENTION

The invention relates to the formation of novel in vivo combinatorial enzyme complexes for use in screening candidate drug agents for bioactivity.

BACKGROUND OF THE INVENTION

Signaling pathways in cells often begin with an effector stimulus that leads to a phenotypically describable change in cellular physiology. Despite the key role intracellular signaling pathways play in disease pathogenesis, in most cases, little is understood about a signaling pathway other than the initial stimulus and the ultimate cellular response.

Historically, signal transduction has been analyzed by biochemistry or genetics. The biochemical approach dissects a pathway in a "stepping-stone" fashion: find a molecule that acts at, or is involved in, one end of the pathway, isolate assayable quantities and then try to determine the next molecule in the pathway, either upstream or downstream of the isolated one. The genetic approach is classically a "shot in the dark": induce or derive mutants in a signaling pathway and map the locus by genetic crosses or complement the mutation with a cDNA library. Limitations of biochemical approaches include a reliance on a significant amount of pre-existing knowledge about the constituents under study and the need to carry such studies out in vitro, post-mortem. Limitations of purely genetic approaches include the need to first derive and then characterize the pathway before proceeding with identifying and cloning the gene.

Screening molecular libraries of chemical compounds for drugs that regulate signal systems has led to important discoveries of great clinical significance. Cyclosporin A (CsA) and FK506, for examples, were selected in standard pharmaceutical screens for inhibition of T-cell activation. It is noteworthy that while these two drugs bind completely different cellular proteins—cyclophilin and FK506 binding protein (FKBP), respectively, the effect of either drug is virtually the same—profound and specific suppression of T-cell activation, phenotypically observable in T cells as inhibition of mRNA production dependent on transcription factors such as NF-AT and NF-κB. Libraries of small peptides have also been successfully screened in vitro in assays for bioactivity. The literature is replete with examples of small peptides capable of modulating a wide variety of signaling pathways. For example, a peptide derived from the HIV-1 envelope protein has been shown to block the action of cellular calmodulin.

A major limitation of conventional in vitro screens is delivery. While only minute amounts of an agent may be necessary to modulate a particular cellular response, delivering such an amount to the requisite subcellular location necessitates exposing the target cell or system to relatively massive concentrations of the agent. The effect of such concentrations may well mask or preclude the targeted response.

In addition, traditional methods do not allow the creation of completely new enzymatic pathways.

Thus, it is an object of the present invention to provide methods and compositions for the effective introduction of enzymatic libraries into cells to screen and create bioactive compounds.

SUMMARY OF THE INVENTION

In accordance with the outlined objects, the present invention provides cells containing a composition comprising an exogeneous scaffold comprising at least a first binding site and a second binding site; and at least a first and a second enzyme. At least one of the enzymes is heterologous to the cell. The first enzyme is bound to said first binding site and said second enzyme is bound to said second binding site.

In a further aspect, the present invention provides cells containing a composition comprising nucleic acid encoding an exogeneous scaffold comprising at least a first binding site and a second binding site; and nucleic acid encoding at least a first and a second enzyme. At least one of the enzymes is heterologous to the cell, and the first enzyme is capable of being bound to the first binding site and the second enzyme is capable of being bound to the second binding site.

In an additional aspect, the invention provides methods of screening for a bioactive agent, comprising expressing in a plurality of host cells nucleic acid encoding an exogeneous scaffold comprising at least a first binding site and a second binding site, and nucleic acids encoding at least a first enzyme and a second enzyme; under conditions where the nucleic acids are expressed, and the first enzyme binds to the first binding site and the second enzyme binds to the second binding site. The method further comprises screening the host cells for a cell exhibiting an altered phenotype, wherein the altered phenotype is due to the presence of a bioactive agent.

In a further aspect, the invention provides methods of screening for a bioactive agent comprising expressing in a plurality of host cells a library of nucleic acids encoding a library of scaffolds, each scaffold comprising at least a first binding site and a second binding site. The method further comprises expressing in the cells a library of nucleic acids encoding a library of enzymes; under conditions where the nucleic acids are expressed, and at least some of the enzymes bind to the scaffolds, followed by screening of the host cells for an altered phenotype.

In an additional aspect, the invention provides compositions comprising a scaffold comprising at least a first and a second binding site; and at least a first and a second enzyme. The first enzyme is bound to the first binding site and the second enzyme is bound to the second binding site, wherein the enzymes do not biologically react with said scaffold or each other.

BRIEF DESCRIPTION OF THE DRAWINGS

FIG. 1A depicts a linear scaffold with enzymes containing exogeneous binding sequences (A*, B* and C*) bound to binding sites (a', b' and c'), wherein the binding sequences are attached to the enzymes via linkers. The scaffold is a linear scaffold. FIG. 1B depicts a scaffold-less system, wherein the binding sequences on the enzymes (A*, B*, C*, D* etc.) are depicted as internal, although as will be appreciated by those in the art, they could be exogeneous and attached via linkers as well.

FIGS. 2A, 2B, 2C, 2D, 2E and 2F depict various scaffold-enzyme possibilities.

FIG. 3 depicts a linear scaffold.

FIGS. 4A, 4B, 4C and 4D depicts various circular scaffolds.

FIGS. 5A and 5B depict systems utilizing transmembrane anchoring sequences, either without a scaffold (FIG. 5A) or with a scaffold (FIG. 5B), although as will be appreciated by those in art, FIG. 5B does not require a scaffold if the binding sequences associate.

FIG. 6 depicts a schematic of a retroviral construct.

DETAILED DESCRIPTION OF THE INVENTION

Figure 1A:
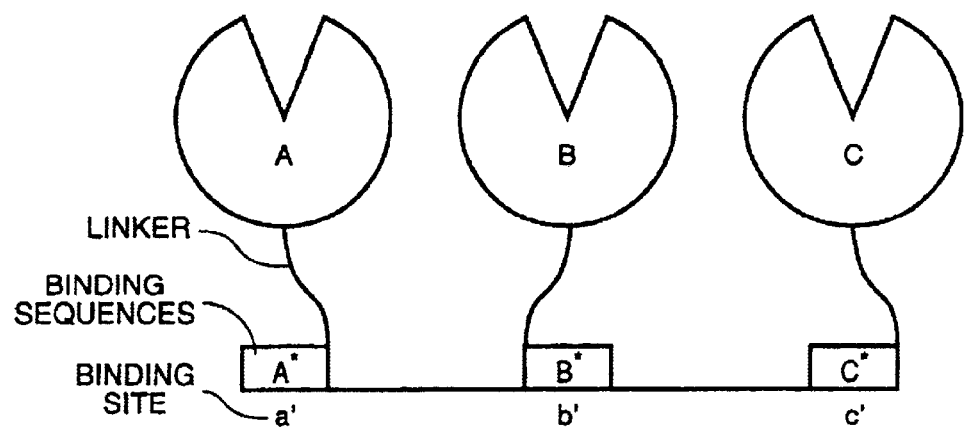
FIGS. 1A and 1B depict different compositions of the invention.

The present invention provides compositions of novel mixtures of enzymes in a spatially constricted or defined manner, i.e. by binding of the enzymes to a scaffold molecule, which allows the enzymes to act on a precursor molecule in novel or efficient ways to form candidate bioactive agents which may then be screened for bioactivity.

As is known in the art, there are a number of enzymatic pathways or cascades wherein the reactant of one enzymatic reaction is the precursor of the next enzymatic reaction, which after catalysis serves as the precursor for yet a third enzyme, etc. It has been suggested that the enzymes of these pathways might be or could be spatially oriented in an organized manner such that productive reactions are maximized and side reactions are minimized. However, these same mixtures of enzymes in the absence of spatial orientation may result in the generation of no product or a highly heterogeneous mixture of products that may be difficult to analyze, with interesting products being made in low concentrations. Thus, the ability to restrict the spatial conformation of the enzyme mixture can result in a more defined mixture of products at higher concentrations. In one embodiment, the present invention provides such spatial constriction.

The ability to make enzyme compositions comprising any number of enzymes from a variety of different organisms in any number of spatially constricted conformations can result in the generation of a large number of novel products which then may be screened for desired biological activities. The number and type of enzymes may be varied, as well as the orientation of the enzymes, thus providing a combinatorial approach.

Thus, the invention generally provides for compositions of a number of enzymes, each bound to a scaffold. A library of enzymes, each of which binds a corresponding binding site on a scaffold, is used. The binding sites may be randomly combined in any number of scaffolds, in any number of orientations, providing a library of scaffolds. Thus, for example, starting with a list of 100 enzymes, and 100 binding sites, each of which will bind one of the enzymes, a large number of scaffolds can be made. Thus, for example, a linear scaffold containing seven binding sites can be configured in $100^7$ different ways. If only seven enzymes are included, a library of $7^7$ different scaffolds, and thus $7^7$ different enzyme complexes can be made, etc. In addition, non-linear scaffolds, as are more fully described below, allow an even greater number of orientations.

These scaffolds, and the corresponding enzymes, are then introduced into a variety of different types of cells, generally using retroviral introduction of the nucleic acids encoding them. Precursor molecules may then be added, and then the cells screened for desired phenotypes. The exact composition of the enzyme mixture, as well as the orientation of the enzymes with respect to both each other and the precursor upon which the enzymes act, may be important in both eliminating undesirable reactions and products as well as obtaining the desired reactants.

Thus the present invention provides methods of using the novel compositions in screening methods for the synthesis, identification and detection of bioactive agents which are capable of altering the phenotype of cells containing the agents. The present invention enables the production of these spatially constricted enzymes, followed by screening of candidate agents, within the same cells. This is different from traditional combinatorial approaches which require the synthesis of the candidate bioactive agents, for example synthetically, followed by the exogeneous addition of the agent to a population of cells to test for bioactivity. Accordingly, the present invention confers a significant advantage since a major limitation of conventional in vitro screens is delivery. While only minute amounts of an agent may be necessary to modulate a particular cellular response, delivering such an amount to the requisite subcellular location necessitates exposing the target cell or system to relatively massive concentrations of the agent. The effect of such concentrations may well mask or preclude the targeted response. In addition, delivery of the agent to the required subcellular location, even at high extracellular concentrations, may be poor.

Thus, the methods of the present invention provide a significant improvement over conventional screening techniques, as they allow the rapid screening of large numbers of candidate bioactive agents in a single, in vivo step. In addition, the present methods allow screening for drugs that can treat disease conditions, in the absence of significant prior characterization of the cellular defects per se.

Accordingly, the present invention provides compositions comprising a scaffold and at least two enzymes. By "scaffold" herein is meant a sequence to which a plurality of enzymes may bind. Scaffolds may be either proteins, and bind enzymes via proteinprotein interactions, or nucleic acids, and bind enzymes via protein-nucleic acid interactions, with protein scaffolds being preferred. "Proteins" in this context includes proteins, oligopeptides and peptides. "Nucleic acids" or "oligonucleotides" in this context includes DNA, RNA, and synthetic nucleic acids. When the scaffold is nucleic acid, it will generally contain phosphodiester bonds, although in some cases, as outlined below, a nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone may be done to increase the stability and half-life of such molecules in physiological environments. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xathanine and hypoxathanine, etc. In a preferred embodiment, for example when nucleic acid encoding the scaffold is introduced into cells, the nucleic acid is DNA.

The scaffold comprises a plurality of binding sites, each of which will bind an enzyme. Thus, for example, a scaffold with two binding sites will bind two enzymes; a scaffold with three binding sites will bind three enzymes; etc. That is, as is generally depicted in the Figures, enzyme A will bind to binding site a, enzyme B will bind to binding site b, etc. Preferably, any single scaffold does not contain more than one binding site for a particular enzyme; that is, the enzyme complexes of the invention preferably contain different enzymes. Scaffolds preferably bind at least two enzymes, with scaffolds that bind from about 2 to about 20 enzymes are preferred, and scaffolds that bind from about 3 to about 10 enzymes being especially preferred, and from about 4 to about 8 being particularly preferred. Generally, each binding site comprises from about 2 to about 20 amino acid residues or from about 2 to about 25 nucleotides.

The actual sequence of the binding sites will be determined in any number of ways, as will be appreciated by those in the art, and will depend on the enzyme, or the part of the enzyme, or a tag added to the enzyme, to which it will bind. In a preferred embodiment, desirable enzymes, as outlined below, may be run in the yeast or mammalian two-hybrid system to determine binding sites.

Alternatively, exogeneous binding sequences can be added to the enzymes. A "binding sequence" is a sequence that will bind to at least one binding site, defined above, or to another binding sequence. Binding sequences and binding sites together form "binding pairs", although the term "binding pair" is not meant to exclude systems that have more than two components. Thus, rather than determine binding sites on the basis of the wildtype sequence of the enzyme, an exogeneous binding sequence can be added to the enzyme, as will be appreciated by those in the art. This may be done directly or through the use of linkers, as defined herein and shown in FIG. 1A. Similarly, as is described below, enzymes each containing a binding sequence to at least one other enzyme may be generated, thus eliminating the need for the scaffold; see FIG. 1B. Furthermore, the enzyme complex may be a mixture of these systems, where some enzymes are bound to scaffolds and other enzymes are associated with the bound enzymes and not to the scaffold. Suitable binding sequences/binding site pairs (or binding sequence/binding sequence pairs, when scaffold binding sites are not used) include any number of known proteinaceous binding pairs including epitopes, ligand-receptor sequences, signaling sequences, etc., which may be used as will be appreciated by those in the art.

In addition, more than one binding site may be generated for each enzyme. That is, binding sites for different surfaces of an enzyme may be made, to hold the enzyme on the scaffold in a variety of conformations. That is, binding sites may be used to different surfaces on the enzyme. For example, binding sites which would bind the active site of the enzyme, thus effectively sterically hindering enzyme function, are not preferred. Similarly, one binding site may be modified to orient the enzyme in a certain way on the scaffold. And, as outlined herein, the binding sites may be placed in different order within a linear or circular scaffold.

Once a binding site for each desired enzyme is determined, the binding sites may be combined into scaffolds in any number of ways. Generally, binding sites are joined together with linker sequences to form scaffolds. The linker sequences may comprise structural elements if desired. For example, when the binding sites are proteins, linker sequences may be chosen to form alpha-helices, β-sheets, turns (i.e. proline rich areas, etc). or other known protein structures. Similarly, when the binding sites are nucleic acid sequences, linker sequences that form known structures such as hairpin loops, stem-loop structures, etc.

Furthermore, linkers may be used to "channel" substrates and reaction products between enzymes, to alter reaction kinetics, for example.

In a preferred embodiment, the binding sites may be held in a particular structural conformation through the use of presentation structures. By "presentation structure" or grammatical equivalents herein is meant a sequence, which, when fused to binding sites, causes the binding sites to assume a conformationally restricted form. Proteins interact with each other largely through conformationally constrained domains. Although small peptides with freely rotating amino and carboxyl termini can be useful, the presentation of peptides in conformationally constrained structures will likely lead to higher affinity interactions of the peptide with the target enzyme. This fact has been recognized in the combinatorial library generation systems using biologically generated short peptides in bacterial phage systems. A number of workers have constructed small domain molecules in which one might present randomized peptide structures.

While the scaffolds and binding sites include nucleic acids or peptides, presentation structures are preferably used with peptide binding sites and scaffolds. Thus, synthetic presentation structures, i.e. artificial polypeptides, are capable of presenting a binding site peptide or scaffold as a conformationally-restricted domain. Generally such presentation structures comprise a first portion joined to the N-terminal end of the peptide, and a second portion joined to the C-terminal end of the peptide; that is, the peptide is inserted into the presentation structure, although variations may be made, as outlined below. To increase the functional isolation of the scaffold, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the binding site on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows: MGC<u>AALESEVSALESEVASLESEVAAL</u>GRGD-MP<u>LAAVKSKLSAVKSKLASVKSKLAA</u>CGPP (SEQ ID NO:1). The underlined regions represent a coiled-coil leucine zipper region defined previously (see Martin et al., EMBO J. 13(22):5303–5309 (1994), incorporated by reference). The bolded GRGDMP region represents the loop structure and when appropriately replaced with binding sites (generally depicted herein as (X)n, where X is an amino acid residue and n is an integer of at least 5 or 6) can be of variable length. The replacement of the bolded region is facilitated by encoding restriction endonuclease sites in the underlined regions, which allows the direct incorporation of binding site oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two binding site regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $K_d=10^{-7}$, for the pro-inflammatory cytokine IL-6.

A preferred minibody presentation structure is as follows: MGRNSQATS<u>GFTFSHF</u>YMEWVRGGEYIAASR <u>HKHNKY</u>TTEYSASVKGRYIVSRDTSQSILYLQKKKG-PP (SEQ ID NO:2). The bold, underline regions are the regions which may be replaced by binding sites. The italized phenylalanine must be invariant in the first region. The entire peptide is cloned in a three-oligonucleotide variation of the coiled-coil embodiment, thus allowing two different regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. As will be appreciated by those in the art, any number of scaffold or binding site sequences, with or without spacer or linking sequences, may be flanked with cysteine residues. In other embodiments, effective presentation structures may be generated by the binding site regions themselves. For example, the regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

The conformation of the scaffold may vary widely, as will be appreciated by those in the art. Scaffolds may be linear, branched, or cyclic. In addition, as will be appreciated by those in the art, each scaffold may comprise more than one molecule, i.e. be comprised of multiple scaffold segments. Any number of molecules may be associated to form the scaffolds of the invention, as is generally depicted in FIGS. 1 and 2.

In a preferred embodiment, the scaffolds are linear, as is generally depicted in FIG. 3. FIG. 3 depicts a scaffold with seven binding sites, although scaffolds with more or less binding sites may be used as well. The binding sites are depicted with small letters, and the associated enzymes with capital letters. As will be appreciated by those in the art, linear scaffolds may assume a non-linear tertiary structure in solution, determined by the structure of the binding sites themselves, linker sequences, the binding of enzymes or tags, the environment (including pH, hydration, solvent, salts, proteins, cellular compartment, etc.), or additional elements either endogenous or exogenous to the environment.

In a preferred embodiment, the scaffolds are cyclic. Cyclic scaffolds, such as are generally depicted in FIGS. 4A, 4B, 4C and 4D, may be made as will be appreciated by those in the art. Protein scaffolds may utilize terminal or internal cysteine residues, that form disulfide bonds under physiological conditions, to form cyclic protein scaffolds (FIGS. 4A and 4B). Cyclic nucleic acid scaffolds utilize regions of complementarity to form cyclic scaffolds (FIG. 4C and 4D). Alternatively, cyclic scaffolds may be constructed using overlapping segments, as is described below. Cyclic scaffolds may also be linked enzymatically, either using endogeneous or exogenous enzymes, or chemical crosslinking processes.

In a preferred embodiment, scaffolds comprising multiple segments are used, as is generally depicted in FIG. 2. In this embodiment, generally a scaffold segment will comprise at least one binding site and at least one connection site. However, as depicted in FIGS. 2A and 2B, some segments may comprise only connection sites. A connection site is used to connect or associate different scaffold segments together, in a manner similar to the association of enzymes and binding sites. Thus, when the scaffolds are nucleic acids, each connection site may comprise areas of sequence complementarity to other connection sites. When the scaffolds are proteins, each connection site may be a sequence that will bind to one or more other protein sequences.

The connection sites may be all the same, such that aggregation of all the connection sites on all segments occurs, for example as is shown in FIG. 2E, or may be different, for example as is shown in FIG. 2F. As will be appreciated by those in the art, a wide variety of different scaffolds comprising multiple segments of binding sites and connection sites are possible.

When the novel compositions are introduced into cells as is outlined below, the scaffolds are preferably exogenous scaffolds. By "exogenous scaffold" herein is meant that the scaffold either a) does not naturally occur within the cell, or b) does naturally occur within the cell but is present at a either a significantly higher concentration than is normally seen within the cell or in a form not normally seen in the cell; e.g. is a portion of a naturally occurring protein or nucleic acid sequence. In a preferred embodiment, the exogeneous scaffolds are synthetic; i.e. they do not naturally occur in nature. In some embodiments, it may be possible to alter endogenous scaffolds such as actin chemically to produce novel scaffolds.

Each binding site of the scaffold binds an enzyme to form an "enzyme complex" or "enzyme-scaffold complex". The binding or association of the enzymes to the scaffolds is preferably non-covalent, yet will be strong enough to cause the binding of the enzymes to the scaffold under physiological conditions, i.e. inside cells or subcellular compartments. That is, the affinity of the binding sites and the enzymes will be strong enough to cause self-aggregation or induced aggregation. Preferably, the association is strong enough to allow purification of the whole scaffold-enzyme complex as a unit, for example by purifying one of the components, immunoprecipitating one or more of the enzymes.

As will be appreciated by those in the art, any number of different enzymes will be used. The enzymes may be from any organisms, including prokaryotes and eukaryotes, with enzymes from bacteria, fungi, extremeophiles, animals (particularly mammals and particularly human) and birds all possible. Suitable classes of enzymes include, but are not limited to, hydrolases such as proteases, carbohydrases, lipases; isomerases such as racemases, epimerases, tautomerases, or mutases; transferases, kinases and phophatases. Preferred enzymes include those that carry out group transfers, such as acyl group transfers, including endo- and exopeptidases (serine, cysteine, metallo and acid proteases); amino group and glutamyl transfers, including glutaminases, γ glutamyl transpeptidases, amidotransferases, etc.; phosphoryl group transfers, including phosphotases, phosphodiesterases, kinases, and phosphorylases; nucleotidyl and pyrophosphotyl transfers, including carboxylate, pyrophosphoryl transfers, etc.; glycosyl group transfers; enzymes that do enzymatic oxidation and reduction, such as dehydrogenases, monooxygenases, oxidases, hydroxylases, reductases, etc.; enzymes that catalyze eliminations, isomerizations and rearrangements, such as elimination/addition of water using aconitase, fumarase, enolase, crotonase, carbon-nitrogen lyases, etc.; and enzymes that make or break carbon-carbon bonds, i.e. carbanion reactions. Suitable enzymes are listed in the Swiss-Prot enzyme database.

The enzymes may be naturally occuring or variant forms of the enzymes. As will be appreciated by those skilled in the art, the potential list of suitable enzyme targets is quite large, and is only limited by the ability to obtain all or part of the nucleic acid or protein sequences, preferably the nucleic acids encoding the enzymes.

In a preferred embodiment, the enzymes are exogeneous (heterologous) to the host cells used. That is, the enzymes are not normally expressed within the cell type, although as will be appreciated by those in the art, an endogeneous copy of the nucleic acid encoding the enzyme may be within the genome of the cell. Generally, in a preferred embodiment, neither the nucleic acid encoding the enzyme, or the enzyme itself, is endogeneous to the cell.

Figure 1B:
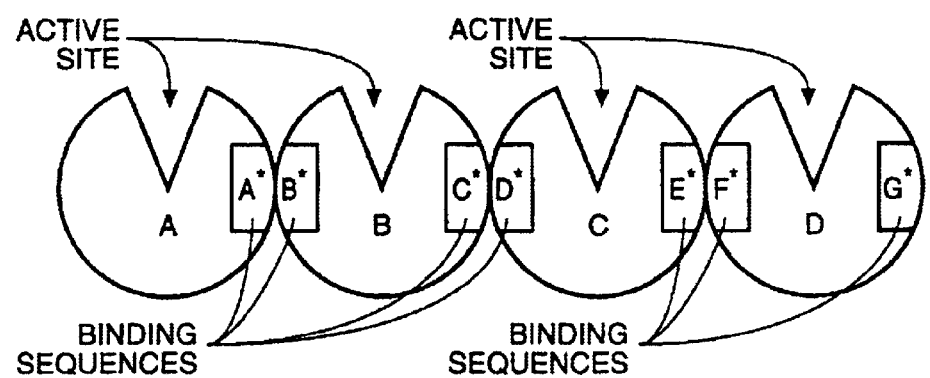

In one embodiment, the system is chosen such that no exogeneous scaffold is required. In one embodiment, the enzymes are all associated through the use of binding sequences (either endogeneous or exogeneous to the enzyme) as is shown in FIG. 1B.

Alternatively, an endogeneous structure serves as the scaffold. Thus, for example, in the case where membrane anchoring sequences such as all or part of a transmembrane domain, are used, such that the enzymes are associated with a membrane, an exogeneous scaffold may not be needed. There may be sufficient concentration and/or association of the enzymes within the two dimensional surface of a membrane that no additional scaffold is needed. This may be useful due to the relatively large size, and therefore low diffusion coefficients, of enzymes within either two or three dimensional space. Similarly, this concentration effect may be increased when targeting occurs to subcellular organelles, as described below. As will be appreciated by those in the art, systems may be generated with the enzyme active sites on the outside (extracellular) of the cell, or on the inside (intracellular), or, in the case of bacteria such as E. coli, within the periplasmic space. Alternatively, the system may be designed to have the enzymes concentrate (again, on either side of the membrane) in a subcellular organelle membrane such as the ER, Golgi, mitochondria, lysosome, chloroplast, etc., or in general endocytotic vesicles.

In this embodiment, when exogeneous scaffolds are not used, at least about two exogeneous enzymes are used, with at least about 3 being preferred, and at least about 4–10 being particularly preferred. In this embodiment, it is preferred, but not required, that at least one of the enzymes has a targeting sequence, preferably a membrane anchoring sequence. If only a subset of the enzymes have a membrane anchoring sequence, the rest of the enzymes will have at least one exogeneous binding sequence.

In one embodiment, the binding sequence is on the same side of the membrane as the enzyme's active site, as is generally depicted in FIG. 5A. Alternatively, the binding sequence is on the other side of the membrane from the enzyme's active site, as is generally depicted in FIG. 5B.

The scaffolds and enzymes are the expression products of nucleic acids. That is, scaffold nucleic acids encode scaffolds, and enzyme nucleic acids encode enzymes. When the scaffold is a nucleic acid, the scaffold is a transcription product of the nucleic acid. When the scaffold is a protein, the scaffold is a translation product of the nucleic acid.

Thus, the present invention provides scaffolds and enzymes, and nucleic acids encoding them. As is more generally described below, a nucleic acid of the invention may encode a single enzyme or a single scaffold, or combinations of enzymes and/or scaffolds. Thus, nucleic acids encoding two or more enzymes, an enzyme and a scaffold, etc., can be made. Thus, the invention provides libraries of scaffolds and libraries of enzymes. In general, as is more fully described below, the limit on the number of components on a single nucleic acid will be determined by the size of the nucleic acid which may be conveniently introduced into a cell. Thus, for example, when retroviral or adenoviral vectors are used, there may be limits on the size of the nucleic acids which may be packaged into viral particles.

In addition to the coding sequences for the scaffolds and enzymes, the nucleic acids of the invention may include fusion partners. By "fusion partner" herein is meant a sequence that is associated either with the nucleic acid or the expression product that confers a common function or ability. Fusion partners can be heterologous (i.e. not native to the host cell), or synthetic (not native to any cell). Suitable fusion partners include, but are not limited to: 1) targeting sequences, defined below, which allow the localization of the scaffolds and enzymes into a subcellular or extracellular compartment; 2) rescue sequences, as defined below, which allow the purification or isolation of either the scaffolds and enzymes or the nucleic acids encoding them; 3) stability sequences, which confer stability or protection from degradation to the scaffolds and enzymes or the nucleic acids encoding them, for example resistance to proteolytic degradation; or 4) combinations of any of 1), 2) and 3).

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and effectors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via either membrane anchoring sequences or secretory signal sequences.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val (SEQ ID NO:3)), Kalderon (1984), et al., Cell, 39:499–509; the human retinoic acid receptor-β nuclear localization signal (ARRRRP (SEQ ID NO:4)); NFκB p50 (EEVQRKRQKL (SEQ ID NO:5); Ghosh et al., Cell 62:1019 (1990); NFκB p65 (EEKRKRTYE (SEQ ID NO:6); Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp SEQ ID NO;7)), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound enzyme-scaffold complexes are useful for both the identification of important elements in these processes as well as for the discovery of effective inhibitors. The invention provides methods for presenting the enzyme complexes of the invention extracellularly or in the cytoplasmic space. For extracellular presentation, a membrane anchoring region is provided at the carboxyl terminus of the expression product. The expression product (i.e. the enzyme, scaffold, or the enzyme complex) is expressed on the cell surface and presented to the extracellular space, such that it can bind to other surface molecules (affecting their function) or molecules present in the extracellular medium. Similarly, the expression product could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:8); Nakauchi et al., PNAS USA 82:5126 (1985) and 1–21 in the case of ICAM-2 (MSSFGYRTLTVALFTLICCPG (SEQ ID NO:9); Staunton et al., Nature (London) 339:61 (1989)). These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPEDCRPRGSVKGTGLDFACDIYIWAPLAGICVA-LLLSLIITLICYHSR (SEQ ID NO:10); Nakauchi, supra) and 224–256 from ICAM-2 (MVIIVTVVSVLLSLFVTS-VLLCFIFGQHLRQQR (SEQ ID NO:11); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO:12), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:13) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the coding region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL (SEQ ID NO:14), with the bold cysteines being palmitolyated; Stoffel et al., J. Biol. Chem 269:27791 (1994)); from rhodopsin (KQFRNCMLTSLCCGKNPLGD (SEQ ID NO:15); Barnstable et al., J. Mol. Neurosci. 5(3):207 (1994)); and the p21 H-ras 1 protein (LNPPDESGPGCMSCKCVLS (SEQ ID NO:16); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:17); Dice, Ann. N.Y. Acad. Sci. 674:58 (1992); or lysosomal membrane sequences from Lamp-1 (MLIPIAGFFALAGLVLIVLIAYLIGRKRSHAGYQTI (SEQ ID NO:18), Uthayakumar et al., Cell. Mol. Biol. Res. 41:405 (1995)) or Lamp-2 (LVPIAVGAALAGVLILVLL-AYFIGLKHHHAGYEQF (SEQ ID NO:19), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:20); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:21); Schatz, supra); mitochondrial intermembrane space sequences (yeast cytochrome c1; MFSMLSKR-WAQRTLSKSFYSTATGAASKSGKLTQKLVTAGVAAA-GITASTL- LYADSLTAEAMTA (SEQ ID NO:22); Schatz, supra) or mitochondrial outer membrane sequences (yeast 70 kD outer membrane protein; MKSFITRNKTAIL-ATVAATGTAIGAYYYYNQLQQQQQRGKK (SEQ ID NO:23); Schatz, supra).

The target sequences may also be endoplasmic reticulum sequences, including the sequences from calreticulin (KDEL (SEQ ID NO:24); Pelham, Royal Society London Transactions B; 1–10 (1992)) or adenovirus E3/19K protein (LYLSRRSFIDEKKMP (SEQ ID NO:25); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO:26), with the bold cysteine farnesylated; Capon, supra); geranylgeranylation sequences (for example, protein rab-5A; LTEPTQPTRNQCCSN (SEQ ID NO:27), with the bold cysteines geranylgeranylated; Farnsworth, PNAS USA 91:11963 (1994)); or destruction sequences (cyclin B1; RTALGDIGN (SEQ ID NO:28); Klotzbucher et al., EMBO J. 1:3053 (1996)).

In a preferred embodiment, the targeting sequence is a secretory signal sequence capable of effecting the secretion of the translation products. There are a large number of known secretory signal sequences which are placed 5' to the coding region of the enzyme or scaffold, and are cleaved from the coding region to effect secretion into the extracellular space. Secretory signal sequences and their transferability to unrelated proteins are well known, e.g., Silhavy, et al. (1985) Microbiol. Rev. 49, 398–418.

Suitable secretory sequences are known, including signals from IL-2 (MYRMQLLSCIALSLALVTNS (SEQ ID NO:29); Villinger et al., J. Immunol. 155:3946 (1995)), growth hormone (MATGSRTSLLLAFGLLCLPWLQEG-SAFPT (SEQ ID NO:30); Roskam et al., Nucleic Acids Res. 7:30 (1979)); preproinsulin (MALWMRLLPLLALLAL-WGPDPAAAFVN (SEQ ID NO:31); Bell et al., Nature 284:26 (1980)); and influenza HA protein (MKAKLLVLLYAFVAGDQI (SEQ ID NO:32); Sekiwawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows: MGLTSQLLPPLFFLLA-CAGNFVHG (SEQ ID NO:33).

In a preferred embodiment, the fusion partner is a rescue sequence. A rescue sequence is a sequence which may be used to purify or isolate either the scaffolds, enzymes, or enzyme complex, or the nucleic acids encoding them. Thus, for example, peptide rescue sequences include purification sequences such as the His$_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the expression products or the nucleic acids encoding them. Thus, for example, peptide scaffolds or enzymes may be stabilized by the incorporation of glycines after the initiation methionine (MG or MGG), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: MG-protein-GGPP.

The fusion partners may be placed anywhere (i.e. N-terminal, C-terminal, internal) in the structure as the biology and activity permits.

In a preferred embodiment, the fusion partner includes a linker or tethering sequence. Linker sequences between various targeting sequences (for example, membrane targeting sequences) and the other components of the constructs (such as the coding regions for the scaffolds and enzymes) may be desirable to allow the proteins to interact with potential targets unhindered. For example, useful linkers include glycine-serine polymers (including, for example, (GS)n, (GSGGS (SEQ ID NO:34))n and (GGGS (SEQ ID NO:35))n, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. In addition, semi-flexible linkers, rather than fully flexible linkers, may also be used. For example, a series of helices, connected by joints, may be used. This may be used to lower the entropy of the system and provide some conformational stability as well. In addition, the linkers may include extender sequences; the linker need not be fully flexible from the point of contact.

In a preferred embodiment, combinations of fusion partners are used. Thus, for example, any number of combinations may be used, with or without linker sequences. As is described herein, using a base vector that contains a cloning site for receiving the enzyme and/or scaffold coding regions, one can cassette in various fusion partners 5' and 3' of the coding region.

In addition to the coding regions of enzymes, scaffolds, and fusion partners, the nucleic acids of the invention may also contain enough extra sequence to effect translation or transcription, as necessary. Thus, for enzymes or protein scaffolds, the nucleic acids generally contain cloning sites which are placed to allow in frame expression of the expression products and fusion partners. When the scaffolds are nucleic acid scaffolds, the nucleic acids encoding the scaffolds will generally be RNA for retroviral delivery, and are generally constructed with an internal CMV promoter, tRNA promoter or cell specific promoter designed for immediate and appropriate expression of the RNA structure at the initiation site of RNA synthesis. The RNA can be expressed anti-sense to the direction of retroviral synthesis and is terminated as known, for example with an orientation specific terminator sequence. Interference from upstream transcription is alleviated in the target cell with the self-inactivation deletion, a common feature of certain retroviral expression systems. Other orientations are possible in some vector systems.

Generally, the nucleic acids of the invention are expressed within the cells to produce expression products of the nucleic acids. As outlined above, the expression products include translation products (i.e. enzymes and protein scaffolds) and transcription products (nucleic acid scaffolds).

The nucleic acids encoding the scaffolds and enzymes are introduced into cells in a variety of ways. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include CaPO$_4$ precipitation, liposome fusion, lipofectin®, electroporation, viral infection, etc. The candidate nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment, the nucleic acids encoding the scaffolds and enzymes are part of retroviral particles which infect the cells. As outlined above, each retroviral particle may contain a single construct, i.e. one enzyme or one scaffold, or more than one, depending on the size of the vector. For example, retroviruses allow generally 7–8 kb, adenoviruses allow up to 30 kb, and herpes viruses can allow up to 100 kb. The constructs may also be set up as "operon" type expression vectors, for example, when co-selection of markers or tags are desirable. Infection can be optimized such that each cell generally expresses a single construct, two constructs, etc., depending on what is required, using the ratio of virus particles to number of cells. Infection is carried out such that preferably each cell gets nucleic acid encoding at least one scaffold and at least some, preferably all, of the enzymes binding to the binding sites of that scaffold. Infection generally follows a Poisson distribution. Generally, infection of the cells is straightforward with the application of the infection-enhancing reagent polybrene, which is a polycation that facilitates viral binding to the target cell.

In a preferred embodiment, the nucleic acids encoding the scaffolds and enzymes are introduced into the cells using retroviral vectors. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins—gag, pol, and env—that are required for packaging, processing, reverse transcription, and integration of recombinant genomes. Those RNA molecules that have in cis the ψ packaging signal are packaged into maturing virions. Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al., supra; Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); and WO 94/19478; and references cited therein, all of which are incorporated by reference.

In one embodiment of the invention, the libraries of scaffolds and enzymes are generated in a retrovirus DNA construct backbone, as is generally described herein. Standard oligonucleotide synthesis is done to generate the nucleic acids encoding the scaffolds, using techniques well known in the art (see Eckstein, Oligonucleotides and Analogues, A Practical Approach, IRL Press at Oxford University Press, 1991. Nucleic acids encoding the enzymes are made as is known in the art. Other viruses may also be used, such as Semliki Forest Virus.

Thus, nucleic acid libraries of enzymes and libraries of scaffolds are made. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE. A general schematic of a retroviral construct is depicted in FIG. 6.

The retroviruses may include inducible and constitutive promoters. For example, there are situations wherein it is necessary to induce expression only during certain phases of the selection process. For instance, a scheme to provide pro-inflammatory cytokines in certain instances must include induced expression of the peptides. This is because there is some expectation that over-expressed pro-inflammatory drugs might in the long-term be detrimental to cell growth. Accordingly, constitutive expression is undesirable, and expression is only turned on during that phase of the selection process when the phenotype is required, and then turn off the retroviral expression to confirm the effect or ensure long-term survival of the producer cells. A large number of both inducible and constitutive promoters are known.

In addition, it is possible to configure a retroviral vector to allow inducible expression of retroviral inserts after integration of the vector in target cells; importantly, the entire system is contained within the retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable, and may be used when multiple retroviruses each containing components of the enzyme complex are introduced into a single cell.

In this manner the primers create a library of system components, either of different enzymes or of different scaffolds. The ligation products are then transformed into bacteria, such as E. coli, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T +gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference.

Preferred systems include PhiNX-eco and PhiNX-ampho or similar cell lines, which are two cells lines as follows. The cell lines are based in principle on the BING and BOSC23 cell lines described in WO 94/19478, which are based on the 293T cell line (a human embryonic kidney line transformed with adenovirus Ela and carrying a temperature sensitive T antigen co-selected with neomycin). The unique feature of this cell line is that it is highly transfectable with either calcium phosphate mediated transfection or lipid-based transfection protocols—greater than 50% of 293T cells can be transiently transfected with plasmid DNA. Thus, the cell line could be a cellular milieu in which retroviral structural proteins and genomic viral RNA could brought together rapidly for creation of helper-defective virus. 293T cells were therefore engineered with stably integrated defective constructs capable of producing gag-pol, and envelope protein for either ecotropic or amphotropic viruses. These lines were called BOSC23 and Bing, respectively. The utility of these lines was that one could produce small amounts of recombinant virus transiently for use in small-scale experimentation. The lines offered advantages over previous stable systems in that virus could be produced in days rather than months.

Two problems became apparent with these first generation lines over the two years they have been in wide use. First, gag-pol and envelope expression was unstable and the lines required vigilant checking for retroviral production capacity; second the structure of the vectors used for protein production were not considered fully "safe" for helper virus production; and third, one of the lines was shown to be inadvertently carrying a hygromycin-containing retrovirus. Although the BING and BOSC23 lines are useful in the present invention, all of these potentially problematic issues are addressed in the PhiNX second-generation lines. These lines are based on 293T cells as well, with the following improvements. First, the ability to monitor gag-pol production on a cell-by cell basis was made by introducing an IRES-CD8 surface marker expression cassette downstream of the reading frame of the gag-pol construct (other surface markers besides CD8 are also useful). IRES (internal ribosome entry site) sequences allow secondary or tertiary protein translation from a single mRNA transcript. Thus, CD8 expression is a direct reflection of intracellular gag-pol and the stability of the producer cell population's ability to produce gag-pol can be readily monitored by flow cytometry. Second, for both the gag-pol and envelope constructs non-Moloney promoters were used to minimize recombination potential with introduced retroviral constructs, and different promoters for gag-pol and envelope were used to minimize their inter-recombination potential. The promoters used were CMV and RSV. Two cell lines were created, PhiNX-eco (PHOENIX-ECO) and PhiNX-ampho (PHOENIX-AMPHO). Gag-pol was introduced with hygromycin as the co-selectable marker and the envelope proteins were introduced with diptheria resistance as the co-selectable marker. Finally, the cells were screened to find a relatively rare cell type that produced gag-pol and env in a uniform distribution, although this is not required. In addition, a line termed PhiNX-gp has been produced that expresses only gag-pol. This line is available for further pseudotyping of retroviral virions with other envelope proteins such as gibbon ape leukemia virus envelope or Vesicular Stomatitus VSV-G protein, Xenotropic, or retargeting envelopes can also be added.

Both PniNX-eco and PhiNX-ampho were tested for helper virus production and established as being helper-virus free. Both lines can carry episomes for the creation of stable cell lines which can be used to produce retrovirus. Both lines are readily testable by flow cytometry for stability of gag-pol (CD8) and envelope expression; after several months of testing the lines appear stable, and do not demonstrate loss of titre as did the first-generation lines BOSC23 and Bing (partly due to the choice of promoters driving expression of gag-pol and envelope). Both lines can also be used to transiently produce virus in a few days. Thus, these new lines are fully compatible with transient, episomal stable, and library generation for retroviral gene transfer experiments. Finally, the titres produced by these lines have been tested. Using standard polybrene-enhanced retroviral infection, titres approaching or above 107 per ml were observed for both PhiNX-eco and PhiNX-ampho when carrying episomal constructs. When transiently produced virus is made, titres are usually ½ to ⅓ that value.

These lines are helper-virus free, carry episomes for long-term stable production of retrovirus, stably produce gag-pol and env, and do not demonstrate loss of viral titre over time. In additon, PhiNX-eco and PhiNX-ampho are capable of producing titres approaching or above $10^7$ per ml when carrying episomal constructs, which, with concentration of virus, can be enhanced to $10^8$ to $10^9$ per ml.

In a preferred embodiment, the cell lines disclosed above, and the other methods for producing retrovirus, are useful for production of virus by transient transfection. The virus can either be used directly or be used to infect another retroviral producer cell line for "expansion" of the library.

Concentration of virus may be done as follows. Generally, retroviruses are titred by applying retrovirus-containing supernatant onto indicator cells, such as NIH3T3 cells, and then measuring the percentage of cells expressing phenotypic consequences of infection. The concentration of the virus is determined by multipying the percentage of cells infected by the dilution factor involved, and taking into account the number of target cells available to obtain a relative titre. If the retrovirus contains a reporter gene, such as lacZ, then infection, integration, and expression of the recombinant virus is measured by histological staining for lacZ exprssion or by flow cytometry (FACS). In general, retroviral titres generated from even the best of the producer cells do not exceed $10^7$ per ml, unless concentration by relatively expensive or exotic apparatus. However, as it has been recently postulated that since a particle as large as a retrovirus will not move very far by brownian motion in liquid, fluid dynamics predicts that much of the virus never comes in contact with the cells to initiate the infection process. However, if cells are grown or placed on a porous filter and retrovirus is allowed to move past cells by gradual gravitometric flow, a high concentration of virus around cells can be effectively maintained at all times. Thus, up to a ten-fold higher infectivity by infecting cells on a porous membrane and allowing retrovirus supernatant to flow past them has been seen. This should allow titres of $10^9$ after concentration.

The nucleic acids encoding the scaffolds and enzymes, as part of retroviral constructs, are introduced into the cells to screen for the production of bioactive agents capable of altering the phenotype of a cell.

As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described herein, a screen will be set up such that the cells exhibit a selectable phenotype in the presence of a bioactive agent. As is more fully described below, cell types implicated in a wide variety of disease conditions are particularly useful, so long as a suitable screen may be designed to allow the selection of cells that exhibit an altered phenotype as a consequence of the presence of a transdominant bioactive agent within the cell.

Accordingly, suitable host cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference. In one embodiment, the cells may also be genetically engineered, that is, contain exogenous nucleic acid, prior to the introduction of the nucleic acids of the invention.

Thus, the component nucleic acids, encoding scaffolds and enzymes, are introduced into a plurality of cells, and expressed, and the expression products or components then associate to form enzyme-scaffold complexes within the cells. Each cell preferably comprises a different enzyme-scaffold complex.

In a preferred embodiment, a first plurality of cells is screened. That is, the cells into which the component nucleic acids are introduced are screened for an altered phenotype. Thus, in this embodiment, the effect of the bioactive agent is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a different enzyme complex, although as will be appreciated by those in the art, some cells within the library may not contain a retrovirus, and some may contain more than one. When methods other than retroviral infection are used to introduce the component nucleic acids into a plurality of cells, the distribution of component nucleic acids within the individual cell members of the cellular library may vary widely, as it is generally difficult to control the number of nucleic acids which enter a cell during electroporation, etc.

In a preferred embodiment, the component nucleic acids are introduced into a first plurality of cells, and the effect of the enzyme complex is screened in a second or third plurality of cells, different from the first plurality of cells, i.e. generally a different cell type. That is, the effect of the bioactive agents is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the component nucleic acids (for example, when inducible promoters are used), to produce the component expression products, either translation or transcription products.

The cells may then be screened for altered phenotypes. That is, the enzyme complex may act on a endogeneous cellular compound to form a novel bioactive agent that is capable of altering the phenotype of the cell. Alternatively, the bioactive agent may already be present in the cell, but at a concentration too low to show the bioactive effect. Optionally, precursor compounds may be added to the cell, which then may be acted upon by the enzyme complex to form a bioactive agent.

In a preferred embodiment, no precursor compounds are added, and the plurality of cells is screened, as is more fully outlined below, for a cell exhibiting an altered phenotype due to the action of the enzyme complex on an endogeneous compound.

In a preferred embodiment, precursor compounds are added to the cells, and the enzyme complexes either enzymatically alter the precursor to form bioactive agents, or act on endogenous compounds which then interact with the precursor to form bioactive agents. By "bioactive agent" describes any molecule, e.g., protein, oligopeptide, small organic molecule, polysaccharide, polynucleotide, etc., with the capability of directly or indirectly altering a cellular phenotype.

"Candidate bioactive agents", "bioactive agent precursors", "precursors" or grammatical equivalents encompass numerous chemical classes, though typically they are organic molecules, preferably small organic compounds having a molecular weight of more than 100 and less than about 2,500 daltons. Precursors generally comprise functional groups necessary for structural interaction with cellular components such as proteins and nucleic acids, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Precursors are also found among biomolecules including peptides, saccharides, fatty acids, steroids, purines, pyrimidines, derivatives, structural analogs or combinations thereof.

Precursors are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Precursors may also include compounds with known capacities for altering cellular phenotypes but with undesirable side effects. For example, as is more fully described below, some chemotherapeutic agents display unacceptable levels of toxicity. These chemotherapeutic agents may be used as precursors such that the enzyme complexes of the invention may alter their structure in ways that lowers the level of toxicity, etc.

As will be appreciated by those in the art, suitable precursor compounds include a very large number of compounds, including, but not limited to, known pharmacophores and pharmacophore analogs and precursors, including hydantoins (Tet. Lett. 37(7):937 (1996)); pyrazoles and isoxazoles (Tet. Lett. 37(7):1003 (1996); imidazoles (Tet. Lett. 37(6):835 (1996); sulfonamides (Tet. Lett. 37(8):1145 (1996); 4-thiazolidinones (Bioorganic & Med. Chem. Let. 6(6):707 (1996); 4-sulfamoylbenzamides (Bioorganic & Med. Chem. Let. 6(5):559 (1996); 2,6-disubstituted quinolones (Tet. Lett. 37(16):2757 (1996); biphenyl core compounds (Bioorganic & Med. Chem. Let. 4(5):659 (1996); actinomycins (Bioorganic & Med. Chem. Let. 4(5):693 (1996); other quinolones (Tet. Lett 37(27): 4815 (1996); 3-aminothiophenes and heterocyles (Tet. Lett 37(34):6213 (1996); benzodiazepine (Bioorganic & Med. Chem. Let. 6(19):2299 (1996); polyazacyclophane (Tetl. Lett. 37(40:7233 (1996); 5- and 6-membered lactams (Tet. Lett. 38(3):359 (1997); spiroindoline (Tet. Lett. 38(9):1497 (1997); substituted guanidines (Tet. Lett. 38(19):3377 (1997); and compounds described in Tetrahedron 52(13) :4527 (1996); all of which are incorporated by reference.

In a preferred embodiment, the precursors are labelled. By "labelled" herein is meant that the precursor compound is either directly or indirectly labeled with a label which provides a detectable signal, e.g. radioisotope, fluorescers, enzyme, antibodies, particles such as magnetic particles, chemiluminescer, etc.

In addition, the precursors may include precursor targeting sequences. Precursor targeting sequences are functionally similar to the fusion partner targeting sequences, in that they serve to target the precursors to a particular subcellular location.

In general, the precursors are added to the cells prior to screening, generally added to the cell media or added to discs on which the cells are grown, etc. The precursors will be added for a sufficient incubation time, generally from about 0.5 to 24 hours before screening, to allow the enzyme complexes sufficient time to enzymatically alter the precursor into new forms. In one embodiment, when the precursors are proteins or nucleic acids, nucleic acids encoding the precursors may be introduced into to the cells as outlined above for component nucleic acids. The cells are then screened as outlined above to detect the presence of a cell with an altered phenotype.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive agent can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the randomized nucleic acid was introduced; in other embodiments, the altered phenotype is detected in a second cell which is responding to some molecular signal from the first cell.

An altered phenotype of a cell indicates the presence of a bioactive agent. Preferably, the bioactive agent is a trans-dominant bioactive agent. By "transdominant" herein is meant that the bioactive agent indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-κB signaling by binding to IκB-α at a region critical for its function, such that in the presence of sufficient amounts of the peptide (or molecular entity), the signaling pathways that normally lead to the activation of NF-κB through phosphorylation and/or degradation of IκB-α are inhibited from acting at IκB-α because of the binding of the peptide or molecular entity. In another instance, signaling pathways that are normally activated to secrete IgE are inhibited in the presence of peptide. Or, signaling pathways in adipose tissue cells, normally quiescent, are activated to metabolize fat. Or, in the presence of a peptide, intracellular mechanisms for the replication of certain viruses, such as HIV-I, or Herpes viridae family members, or Respiratory Syncytia Virus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In general, cis-effects are effects within molecules wherein elements that are interacting are covalently joined to each other although these elements might individually manifest themselves as separable domains. Trans-effects (transdominant in that under some cellular conditions the desired effect is manifested) are those effects between distinct molecular entities, such that molecular entity A, not covalently linked to molecular entity B, binds to or otherwise has an effect upon the activities of entity B. As such, most known pharmacological agents are transdominant effectors.

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the component nucleic acid, the enzyme complex and/or the bioactive agent is isolated from the positive cell. This may be done in a number of ways. In a preferred embodiment, primers complementary to DNA regions common to the retroviral constructs, or to specific components of the library such as a rescue sequence, defined above, are used to "rescue" the sequences. The enzyme complex may then be reconstructed in vitro, the precursor added, and the reaction products separated, tested, and characterized chemically.

The enzyme complex may be isolated through the use of purification sequences. Thus for example, one or all of the components may contain a purification sequence, such as an epitope tag or the His$_6$ tag. The cells containing the enzyme complex may be lysed and the complex isolated using any number of techniques, including immunoprecipitation or affinity chromatography.

Alternatively, the bioactive agent may be isolated using a label present on the precursor, either by using the label directly or by following the presence of the label in a purification scheme, such as capillary electrophoresis and mass spectroscopy. In some instances, as is outlined below, this may also pull out the primary target molecule, if there is a sufficiently strong binding interaction between the bioactive agent and the target molecule. Alternatively, the bioactive agent may be detected using mass spectroscopy.

Once rescued, the composition of the enzyme complex and the identification of the bioactive agent is determined. This information can then be used in a number of ways.

In a preferred embodiment, the bioactive agent is resynthesized and reintroduced into the target cells, to verify the effect. This may be done in a variety of ways, as will be appreciated by those in the art, and may depend on the composition of the bioactive agent. For example, proteinaceous bioactive agents may be reintroduced using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference. Simply adding the bioactive agent to target cells, in the same way precursor molecules are added, may be sufficient.

In a preferred embodiment, the identification of a bioactive agent is used to generate more bioactive agent precursors. For example, analogs of the bioactive agents may be tested as precursors. It may also be desirable to "walk" around a potential binding site, in a manner similar to the mutagenesis of a binding pocket, by keeping one area of the bioactive agent constant and randomizing the other end to shift the binding of the agent around.

In a preferred embodiment, the bioactive agent is used to identify target molecules, i.e. the molecules with which the bioactive agent interacts. As will be appreciated by those in the art, there may be primary target molecules, to which the bioactive agent binds or acts upon directly, and there may be secondary target molecules, which are part of the signalling pathway affected by the bioactive agent; these might be termed "validated targets".

In a preferred embodiment, the bioactive agent is used to pull out target molecules. For example, rescue or purification sequences may be added to a bioactive agent, which can allow the purification of primary target molecules via biochemical means (co-immunoprecipitation, affinity columns, etc.). Proteinaceous bioactive agents, when expressed in bacteria and purified, can be used as a probe against a bacterial cDNA expression library made from mRNA of the target cell type. Or, proteinaceous bioactive agents can be used as "bait" in either yeast or mammalian two or three hybrid systems. Such interaction cloning approaches have been very useful to isolate DNA-binding proteins and other interacting protein components. It is also possible to synthetically prepare labeled bioactive agent and use it to screen a cDNA library expressed in bacteriophage for those cDNAs which bind the agent. Furthermore, it is also possible that one could use cDNA cloning via retroviral libraries to "complement" the effect induced by the agent. In such a strategy, the agent would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the agent acts upon. The bioactive agent may also be tagged with a crosslinkable tag to bind to the target to allow purification, for example for low affinity interactions.

Once primary target molecules have been identified, secondary target molecules may be identified in the same manner, using the primary target as the "bait". In this manner, signalling pathways may be elucidated. Similarly, bioactive agents specific for secondary target molecules may also be discovered, to allow a number of bioactive agents to act on a single pathway, for example for combination therapies or pathway engineering.

In addition, once a particular enzyme complex has been identified as useful for a particular application, it may be "evolved" using the techniques outlined herein to optimize the system. For example, different scaffolds, different but related enzymes or mutated enzymes, different binding sites or binding sequences, or the same binding sites or sequences in alternative conformations may all be used.

The screening methods of the present invention may be useful to screen a large number of cell types under a wide variety of conditions. As is outlined below, the libraries of enzyme complexes may be introduced into the cells, in the presence or absence of specific precursor compounds, and the cells tested in a variety of ways. Generally, the host cells are cells that are involved in disease states, and they are tested or screened under conditions that normally result in undesirable consequences on the cells. When a suitable bioactive agent is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, enzyme complexes can be introduced into any tumor cell (primary or cultured), and agents identified which by themselves induce apoptosis, cell death, loss of cell division or decreased cell growth. This may be done de novo, or by the introduction of "biased" precursors, such as analogs of known chemotherapeutic agents. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then libraries of enzyme complexes introduced into these cells, to select for bioactive agents which reverse or correct the transformed state. One of the signal features of oncogene transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive agent will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive agents capable of blocking the ability of the growth factor or cytokine to stimulate the tumor cell. The introduction of libraries of enzyme complexes into specific tumor cells with the addition of the growth factor or cytokine, followed by selection of bioactive agents which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have libraries of enzyme complexes introduced into them, and agents selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular activators of this gene could block metastasis, and a screen for its upregulation (by fusing it to a reporter gene) would be of interest. Many oncogenes also enhance metastasis. Agents which inactivate or counteract mutated RAS oncogenes, v-MOS, v-RAF, A-RAF, v-SRC, v-FES, and v-FMS would also act as anti-metastatics. Agents which act intracellularly to block the release of combinations of proteases required for invasion, such as the matrix metalloproteases and urokinase, could also be effective antimetastatics.

In a preferred embodiment, the enzyme complexes of the present invention are introduced into tumor cells known to have inactivated tumor suppressor genes, and successful reversal by either reactivation or compensation of the knock-out would be screened by restoration of the normal phenotype. A major example is the reversal of p53-inactivating mutations, which are present in 50% or more of all cancers. Since p53's actions are complex and involve its action as a transcription factor, there are probably numerous potential ways a bioactive agent could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening of bioactive agents which restore the constitutive function of the brca-1 or brca-2 genes, and other tumor suppressor genes important in breast cancer such as the adenomatous polyposis coli gene (APC) and the *Drosophila* discs-large gene (Dlg), which are components of cell-cell junctions. Mutations of brca-1 are important in hereditary ovarian and breast cancers, and constitute an additional application of the present invention.

In a preferred embodiment, the methods of the present invention are used to create novel cell lines from cancers from patients. An enzyme complex which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Ebstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing enzyme complexes which act to inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Enzyme complexes (and precursors, if necessary) are inserted into cardiomyocytes, the cells are subjected to the insult, and bioactive agents are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the enzyme complexes (and precursors, if necessary), followed by the application of arrythmogenic insults, with screening for bioactive agents that block specific depolarization of cell membrane. This may be detected using patch clamps, or via fluorescence techniques. Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive agents which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias. Bioactive agents are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive agents may be found which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for agents that either: 1) downregulate adhesion molecule expression on the surface of the endothelial cells (binding assay); or 2) block adhesion molecule activation on the surface of these cells (signaling assay).

Embolic phenomena can also be addressed by activating proteolytic enzymes on the cell surfaces of endothelial cells, and thus releasing active enzyme which can digest blood clots. Thus, delivery of the complexes of the invention to endothelial cells is done, followed by standard fluorogenic assays, which will allow monitoring of proteolytic activity on the cell surface towards a known substrate. Bioactive agents can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Enzyme complex libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Enzyme complexes can be inserted into these cell types and their proliferation in response to specific stimuli monitored. One application may be intracellular agents which block the expression or function of c-myc and other oncogenes in smooth muscle cells to stop their proliferation. A second application may involve the expression of libraries in vascular smooth muscle cells to selectively induce their apoptosis. Application of small molecules derived from these systems may require targeted drug delivery; this is available with stents, hydrogel coatings, and infusion-based catheter systems. Agents which downregulate endothelin-1A receptors or which block the release of the potent vasoconstrictor and vascular smooth muscle cell mitogen endothelin-1 may also be candidates for therapeutics. Agents can be isolated from these systems which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Enzyme complexes can be inserted into capillary endothelial cells and their growth monitored. Stimuli such as low oxygen tension and varying degrees of angiogenic factors can regulate the responses, and agents isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find agents that regulate LDL and HDL metabolism. Enzyme complex libraries can be inserted into the appropriate cells (including hepatocytes, mononuclear leukocytes, endothelial cells) and agents selected which lead to a decreased release of LDL or diminished synthesis of LDL, or conversely to an increased release of HDL or enhanced synthesis of HDL. Bioactive agents can also be isolated from enzyme complex libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive agents that regulate or inhibit the responses of neuropeptide Y (NPY), cholecystokinin and galanin receptors, are particularly desirable. Enzyme complex libraries can be inserted into cells that have these receptors cloned into them, and inhibitory agents selected that block the signaling responses to galanin and NPY. In a similar manner, agents can be found that regulate the leptin receptor.

In a preferred embodiment, the present methods are useful in neurobiology applications. Enzyme complex libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield agents which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting libraries into these cells, and then looking for bioactive agents that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with enzyme complex libraries and screened for their growth, proliferation, collagen stimulating activity, and/or proline incorporating ability on the target osteoblasts. Alternatively, enzyme complexes can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Enzyme complexes can be inserted into cells removed from active psoriatic plaques, and bioactive agents isolated which decrease the rate of growth of these cells.

In a preferred embodiment, the present methods are useful in the regulation or inhibition of keloid formation (i.e. excessive scarring). Enzyme complexes are inserted into skin connective tissue cells isolated from individuals with this condition, and bioactive agents isolated that decrease proliferation, collagen formation, or proline incorporation. Results from this work can be extended to treat the excessive scarring that also occurs in bum patients. If a common motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Enzyme candidate libraries can be inserted into skin connective tissue cells, and bioactive agents isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Enzyme complexes can be inserted into melanocytes and known stimuli that increase the synthesis of melanin applied to the cells. Bioactive agents can be isolated that inhibit the synthesis of melanin under these conditions.

In a preferred embodiment, the present methods are useful in endocrinology applications. The enzyme complex technology can be applied broadly to any endocrine, growth factor, cytokine or chemokine network which involves a signaling molecule that acts in either an endocrine, paracrine or autocrine manner that binds or dimerizes a receptor and activates a signaling cascade that results in a known phenotypic or functional outcome. The methods are applied so as to isolate an agent which either mimics the desired hormone (i.e., insulin, leptin, calcitonin, PDGF, EGF, EPO, GMCSF, IL1–17, mimetics) or inhibits its action by either blocking the release of the hormone, blocking its binding to a specific receptor or carrier protein (for example, CRF binding protein), or inhibiting the intracellular responses of the specific target cells to that hormone. Selection of agents which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Enzyme complexes can then be inserted into these cells under the above conditions, and agents isolated which block or diminish the growth and/or release of the virus. As with chemotherapeutics, these experiments can also be done with drugs which are only partially effective towards this outcome, and bioactive agents isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+ mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians.

The action of extracellularly anchored enzyme complexes on precursors could allow increased uptake into the cells, for example.

Viruses are known to enter cells using specific receptors to bind to cells (for example, HIV uses CD4, coronavirus uses CD13, murine leukemia virus uses transport protein, and measles virus uses CD44) and to fuse with cells (HIV uses chemokine receptor). Enzyme complexes can be inserted into target cells known to be permissive to these viruses, and bioactive agents isolated which block the ability of these viruses to bind and fuse with specific target cells.

In a preferred embodiment, the present invention finds use with infectious organisms. Intracellular organisms such as mycobacteria, listeria, salmonella, pneumocystis, yersinia, leishmania, T. cruzi, can persist and replicate within cells, and become active in immunosuppressed patients. There are currently drugs on the market and in development which are either only partially effective or ineffective against these organisms. Enzyme complexes can be inserted into specific cells infected with these organisms (pre- or post-infection), and bioactive agents selected which promote the intracellular destruction of these organisms. In addition agents can be selected which enhance the cidal properties of drugs already under investigation which have insufficient potency by themselves, but when combined with a specific bioactive agent, are dramatically more potent through a synergistic mechanism. Finally, bioactive agents can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Enzyme complexes can be introduced into the specific cell types where specific changes leading to cellular damage or apoptosis by the antibiotics are produced, and bioactive agents can be isolated that confer protection, when these cells are treated with these specific antibiotics.

Furthermore, the present invention finds use in screening for bioactive agents that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Enzyme complexes can be inserted into specific cells derived from kidney cells and cells of the choroid plexus known to have active transport mechanisms for antibiotics. Bioactive agents can then be isolated which block the active transport of specific antibiotics and thus extend the serum halflife of these drugs.

In a preferred embodiment, the present methods are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Enzyme complexes can be introduced into specific cell types with characteristic drug-induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy. In this embodiment, the drug may also act as the precursor.

Drug toxicity may be due to a specific metabolite produced in the liver or kidney which is highly toxic to specific cells, or due to drug interactions in the liver which block or enhance the metabolism of an administered drug. Enzyme complexes can be introduced into liver or kidney cells following the exposure of these cells to the drug known to produce the toxic metabolite. Bioactive agents can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Enzyme complexes can be introduced into tumor cell lines (primary and cultured) that have demonstrated specific or multiple drug resistance. Bioactive agents can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for agents which block the normal efflux of fluorescent drug from these cells. Enzyme complexes are particularly suited to screening for agents which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in 30 first pass metabolism may thus be a useful adjunct enhancing the efficacy of these drugs.

First pass metabolism occurs in the liver, thus inhibitors of the corresponding catabolic enzymes may enhance the effect of the cognate drugs. Reversible inhibitors would be delivered at the same time as, or slightly before, the drug of interest. Screening of enzyme complex libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Enzyme complexes can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select an agent that inhibits T cell subset from recognizing a self-antigen bearing cell); 2) allergic diseases where one wants to decrease the stimulation of IgE producing cells (select an agent which blocks release from T cell subsets of specific B-cell stimulating cytokines which induce switch to IgE production); 3) in transplant patients where one wants to induce selective immunosuppression (select an agent that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Enzyme complexes can be inserted into B cells and bioactive agents selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and IL1–17, may be selected, or agents that bind cytokines such as TNF-α, before they bind their receptor.

Antigen processing by mononuclear leukocytes (ML) is an important early step in the immune system's ability to recognize and eliminate foreign proteins. Enzyme complexes can be inserted into ML cell lines and agents selected which alter the intracellular processing of foreign agents and sequence of the foreign peptide that is presented to T cells by MLs on their cell surface in the context of Class II MHC. One can look for members of the library that enhance immune responses of a particular T cell subset (for example, the agent would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Enzyme complex libraries can be inserted into MLs, mast cells, eosinophils, and other cells participating in a specific inflammatory response, and bioactive agents selected which inhibit the synthesis, release and binding to the cognate receptor of each of these types of mediators.

In a preferred embodiment, the present methods are useful in biotechnology applications. Enzym complex expression in mammalian cells can also be considered for other pharmaceutical-related applications, such as modification of protein expression, protein folding, or protein secretion. One such example would be in commercial production of protein pharmaceuticals in CHO or other cells. Enzyme complexes resulting in bioactive agents which select for an increased cell growth rate (perhaps agents mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Random peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive agent sequence identified can then be coupled to an antibody, enzyme, drug, imaging agent or substance for which organ targeting is desired.

Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e. within a signalling pathway, to localize the effects to a functional area of interest.

All references cited herein are incorporated by reference.

We claim:

1. A method, comprising:
   introducing a library of nucleic acids into cells using a retroviral vector to produce a plurality of cells comprising a plurality of different enzymatic complexes, wherein each cell of said plurality of cells comprises:
   a nucleic acid encoding a non-naturally occurring exogenous linear scaffold comprising a first binding sequence and a second binding sequence; and
   nucleic acids encoding first and second enzymes, each enzyme comprising an exogenous binding sequence, wherein said exogenous binding sequence binds to one of the first and second binding sequences of the scaffold to form an enzymatic complex and wherein said enzymes do not react with said scaffold; and
   screening said plurality of cells for cell exhibiting an altered phenotype wherein the enzymatic complex confers upon the cell an altered phenotype relative to a phenotype of the cell in the absence of said complex.

2. The method of claim 1, further comprising identifying an enzymatic complex that alters the phenotype of cell.

* * * * *